(12) United States Patent
Yen et al.

(10) Patent No.: US 9,421,203 B2
(45) Date of Patent: Aug. 23, 2016

(54) SENSITIZATION OF CANCER CELLS TO DNA DAMAGE BY INHIBITING KINASES ESSENTIAL FOR DNA DAMAGE CHECKPOINT CONTROL

(71) Applicant: Institute for Cancer Research, Philadelphia, PA (US)

(72) Inventors: Timothy Yen, Haverford, PA (US); Neil Beeharry, Philadelphia, PA (US)

(73) Assignee: Institute for Cancer Research, Philadelphia, PA (US)

( * ) Notice: Subject to any disclaimer, the term of this patent is extended or adjusted under 35 U.S.C. 154(b) by 0 days.

(21) Appl. No.: 14/564,186

(22) Filed: Dec. 9, 2014

(65) Prior Publication Data
US 2015/0133466 A1    May 14, 2015

Related U.S. Application Data

(63) Continuation of application No. PCT/US2013/031344, filed on Mar. 14, 2013.

(60) Provisional application No. 61/660,321, filed on Jun. 15, 2012.

(51) Int. Cl.
*A61K 31/496* (2006.01)
*A61K 31/7068* (2006.01)

(52) U.S. Cl.
CPC ............ *A61K 31/496* (2013.01); *A61K 31/7068* (2013.01)

(58) Field of Classification Search
CPC .................................................... A61K 31/496
See application file for complete search history.

(56) References Cited

U.S. PATENT DOCUMENTS

| | | | |
|---|---|---|---|
| 6,002,008 A | 12/1999 | Wissner et al. | |
| 7,070,968 B2 * | 7/2006 | Kufe | A61K 31/365 424/94.5 |
| 7,417,148 B2 | 8/2008 | Boschelli et al. | |
| 7,767,678 B2 | 8/2010 | Tesconi et al. | |
| 7,919,625 B2 | 4/2011 | Boschelli et al. | |
| RE42,376 E | 5/2011 | Wissner et al. | |
| 2003/0082685 A1 | 5/2003 | Weischselbaum et al. | |
| 2007/0010527 A1 | 1/2007 | Boschelli | |
| 2008/0033175 A1 | 2/2008 | Sutherland et al. | |
| 2010/0028346 A1 | 2/2010 | Lutz et al. | |
| 2010/0216828 A1 | 8/2010 | Dierks et al. | |
| 2013/0210024 A1 * | 8/2013 | Yu | A61K 31/122 435/6.18 |

OTHER PUBLICATIONS

Boschelli et al., caplus an 2006:211292.*
Golas-et-al-2, caplus an 2005:513607.*
Goias et al., caplus 2003:72680.*
Bosutinib, 2016, http://www.selleckchem.com/products/Bosutinib.html.*
RN 1428126-92-4, 2013.*
Rajeshkumar, et al., "MK-1775, a Potent Wee1 Inhibitor, Synergizes with Gemcitabine to Achieve Tumor Regressions, Selectively in p53—Deficient Pancreatic Cancer Zenografts", Clin. Cancer Res., 17(9) May 1, 2011, 2799-2806.
Levinson, et al., "Structural and Spectroscopic Anaylsis of the Kinase Inhibitor Bosutinib and an Isomer of Bosutinib Binding to the Abl Tyrosine Kinase Domain", PLoS ONE, 7(4): e29828, doi:10.1371/journal.pone.0029828, 2015.
Golas, et al., "SKI-606, a Src/Abl Inhibitor with In vivo Activity in Colon Tumor Xenograft Models", Cancer Res., 65(12), Jun. 15, 2005, pp. 5358-5364.
International Search Report and Written Opinion issued in related International Application PCT/US2013/031344 dated May 23, 2013.

* cited by examiner

*Primary Examiner* — Sun Jae Yoo
(74) *Attorney, Agent, or Firm* — Stradley Ronon Stevens & Young, LLP

(57) ABSTRACT

The invention provides methods for overriding cell cycle arrest in a tumor cell, which comprise inducing DNA damage in the cell, and contacting the cell with an amount of bosutinib or a bosutinib isomer effective to inhibit one or more kinase constituents of a DNA damage checkpoint pathway. The invention also provides novel bosutinib isomers, as well as compositions of the novel isomers and the bosutinib isomer 3,5-dichloro-4-methoxyaniline.

21 Claims, 10 Drawing Sheets

Fig. 5A

|  | Number of kinases inhibited >50% | % of total kinases inhibited |
|---|---|---|
| Bosutinib-I | 84 | 30.1 |
| Dasatinib | 50 | 17.9 |
| Dovitinib | 65 | 23.3 |
| Erlotinib | 7 | 2.5 |
| Imatinib | 8 | 2.9 |
| Lapatinib | 2 | 0.7 |
| Sunitinib | 90 | 32.3 |

Fig. 5B

% remaining kinase activity

|  | Abl | C-Src | EGFR | VEGFR | Fyn | PDGFR | Yes | Chk1 | Wee1 |
|---|---|---|---|---|---|---|---|---|---|
| Bosutinib-I | 1.8 | 6.1 | 3.8 | 44.5 | 29.4 | 87 | 7.3 | 38.9 | 40.5 |
| Dasatinib | 2.9 | 3.5 | 21.1 | 97.3 | 2.0 | 1.8 | 1.9 | 96 | 92.6 |
| Dovitinib | 24. | 16 | 97.2 | 26.2 | 22.5 | 12.6 | 6.3 | 30.8 | 92 |
| Erlotinib | 52. | 77.4 | 4.2 | 87.5 | 94.7 | 83.4 | 68.3 | 95.1 | 95.2 |
| Imatinib | 44. | 86.5 | 92 | 98.3 | 85.8 | 5.9 | 88.6 | 109.5 | 100.5 |
| Lapatinib | 96. | 102.5 | 8.0 | 100.4 | 99.4 | 107.5 | 84.7 | 100.5 | 97.6 |
| Sunitinib | 47. | 39.8 | 89.2 | 58.7 | 71.3 | 10.9 | 5.9 | 29.2 | 91.8 |

US 9,421,203 B2

SENSITIZATION OF CANCER CELLS TO DNA DAMAGE BY INHIBITING KINASES ESSENTIAL FOR DNA DAMAGE CHECKPOINT CONTROL

CROSS REFERENCE TO RELATED APPLICATIONS

This application is a Continuation of PCT Application No. PCT/US2013/031344, filed on Mar. 14, 2013, and claims priority to U.S. Provisional Application No. 61/660,321, filed on Jun. 15, 2012, the contents of each application are incorporated by reference herein, in their entirety and for all purposes.

STATEMENT OF GOVERNMENT SUPPORT

The inventions described herein were made, in part, with funds obtained from the National Institutes of Health, Grant No. R01 GM086877, and the U.S. Department of Defense, Grant No. OC100172. The U.S. government may have certain rights in these inventions.

FIELD OF THE INVENTION

The invention relates generally to the field of cancer treatment. More particularly, the invention relates to combination therapies for treating cancer cells, and especially for enhancing the susceptibility of cancer cells to death induced by DNA damage.

BACKGROUND OF THE INVENTION

Various publications, including patents, published applications, technical articles and scholarly articles are cited throughout the specification. Each of these cited publications is incorporated by reference herein, in its entirety and for all purposes.

One major mechanism underlying chemotherapy and radiation therapy for treating cancer is the induction of DNA damage. Damaging DNA in the cancer cells ensures that the genome cannot be properly propagated by subsequent cell division and proliferation. DNA damage that cannot be corrected generally induces cell death.

Cancer cells, as with normal cells, have a failsafe mechanism referred to as the DNA damage checkpoint. During cell division, the DNA damage checkpoint prevents cells with damaged DNA to progress through the cell cycle and divide, until that damage is repaired. In cancer cells, the checkpoint mechanism is believed to contribute to drug resistance because it allows the cells to repair their damaged DNA and thus continue to proliferate. Accordingly, overcoming the DNA damage checkpoint is a desirable goal for cancer therapy.

Agents that inhibit the DNA damage checkpoint are believed to enhance killing of cancer cells by DNA damage, particularly for chemotherapeutic agents that induce DNA damage. Currently, the Chk1 and Wee1 kinases are considered desirable targets for the development of DNA damage checkpoint inhibiting agents that may be used in the clinic in combination with other agents or DNA-damaging radiation therapies to improve patient treatment outcomes. There is a need to identify agents that inhibit constituents of the DNA damage checkpoint pathways.

SUMMARY OF THE INVENTION

The invention provides methods for treating tumors in a subject in need thereof. The methods generally comprise the steps of damaging DNA in a cell of the tumor, and administering to the subject an effective amount of authentic bosutinib of Formula I, the bosutinib isomer of Formula II, the bosutinib isomer of Formula IV, or a pharmaceutically acceptable salt of Formula I, Formula II, or Formula IV. An effective amount may be any concentration that inhibits cell cycle arrest in targeted tumor cells. The effective amount of Formula I may be higher than the effective amount of Formula II. Inhibition of cell cycle arrest is preferably caused, enhanced, or facilitated by inhibition of the biologic activity of one or more kinase enzymes that are constituents of a DNA damage checkpoint pathway in the cell cycle. For example, cellular recognition of DNA damage may induce cell cycle arrest to allow for DNA damage to be remedied, and inhibition of this arrest permits the cell cycle to proceed into mitosis with the DNA damage substantially unrepaired.

Damaging DNA in the cell may comprise irradiating the cell in the subject, preferably by targeting the radiation source directly to the tumor or section of the tumor where the target cell is located. Damaging DNA may comprise administering to the subject an effective amount of an agent that damages DNA, and the agent preferably comprises gemcitabine.

The subject may be any animal, such as a mammal, with human beings being highly preferred. The tumor may be a tumor of the pancreas, lung, head and neck, kidney, hematopoietic system, breast, ovary, colon, lymph nodes, bladder, prostate gland, stomach, or esophagus. A tumor of the pancreas is preferred.

The invention also features methods for overriding cell cycle arrest in a tumor cell. The methods may generally comprise damaging DNA in a tumor cell, and contacting the cell with an amount of the bosutinib of Formula I, the bosutinib isomer of Formula II, the bosutinib isomer of Formula IV, or a pharmaceutically acceptable salt of Formula I, Formula II or Formula IV, effective to inhibit one or more of Chk1 and Wee1 in the cell. By inhibiting Chk1, Wee1, or both Chk1 and Wee1 with the bosutinib isomer or pharmaceutically acceptable salt thereof, cell cycle arrest is inhibited such that the cell may proceed through the cell cycle with DNA damage present and substantially unrepaired. Preferably, inhibition of the arrest of cell cycle progression permits the cell to enter the mitosis phase of the cell cycle.

Damaging DNA in the cell may comprises irradiating the cell or contacting the cell with an amount of an agent that damages DNA that is effective for damaging the DNA. The agent may comprise an alkylating agent, may comprise a pyrimidine analog, and preferably comprises gemcitabine.

The tumor cell may be a tumor cell of the pancreas, a tumor cell of the lung, a tumor cell of the head and neck, a tumor cell of the kidney, a tumor cell of the hematopoietic system, a tumor cell of the breast, a tumor cell of the ovary, a tumor cell of the colon, a tumor cell of the lymph nodes, a tumor cell of the bladder, a tumor cell of the prostate gland, a tumor cell of the stomach, or a tumor cell of the esophagus. The method may be carried out in vitro. The method may be carried out in vivo, for example, in a mammal having a tumor of the pancreas, lung, head and neck, kidney, hematopoietic system, breast, ovary, colon, lymph nodes, bladder, prostate gland, stomach, or esophagus.

The invention also features novel bosutinib isomers, having Formula IV. As well, the invention provides compositions comprising authentic bosutinib of Formula I, the bosutinib isomer of Formula II, the bosutinib isomer of Formula IV, or a pharmaceutically acceptable salt of Formula I, Formula II, or Formula IV, and a pharmaceutically acceptable carrier. Authentic bosutinib of Formula I, the bosutinib isomer of Formula II or Formula IV may be present in the composition at a concentration effective for inhibiting Chk1, Wee1, or both Chk1 and Wee1 in a tumor cell. The composition may further comprise an amount of a DNA-damaging agent effective to induce DNA damage in a tumor cell. The composition may further comprise an amount of gemcitabine effective to induce DNA damage in a tumor cell.

The invention also features kits comprising a DNA-damaging agent, authentic bosutinib of Formula I, the bosutinib isomer of Formula II, the bosutinib isomer of Formula IV, or a pharmaceutically acceptable salt of Formula I, Formula II, or Formula IV, and instructions for using the kit in a method for treating a tumor with the DNA-damaging agent and authentic bosutinib, or the bosutinib isomer of Formula II or Formula IV. The DNA damaging agent may comprise an alkylating agent, may comprise a pyrimidine analog, and preferably comprises gemcitabine.

The invention also features methods for enhancing the sensitivity of a tumor cell to gemcitabine. In general, the methods comprise contacting a tumor cell with an amount of gemcitabine effective to induce DNA damage in the cell, and contacting the cell with an amount of authentic bosutinib of Formula I, the bosutinib isomer of Formula II, the bosutinib isomer of Formula IV, or a pharmaceutically acceptable salt of Formula I, Formula II, or Formula IV, effective to inhibit one or more of Chk1 and Wee1. Contacting the cell with authentic bosutinib, or the bosutinib isomer of Formula II or Formula IV preferably enhances the sensitivity of the cell to gemcitabine-induced cell death relative to the level of gemcitabine-induced cell death in a cell of the same type contacted with gemcitabine but not contacted with the bosutinib isomer. Authentic bosutinib of Formula I, and the bosutinib isomer of Formula II or Formula IV may reduce the $LC_{50}$ of gemcitabine to less than about 10 nM. Authentic bosutinib of Formula I, and the bosutinib isomer of Formula II or Formula IV may reduce the $LC_{50}$ of gemcitabine to less than about 5 nM. Authentic bosutinib of Formula I, and the bosutinib isomer of Formula II or Formula IV may reduce the $LC_{50}$ of gemcitabine to about 3 nM or less.

The tumor cell may be a tumor cell of the pancreas, a tumor cell of the lung, a tumor cell of the head and neck, a tumor cell of the kidney, a tumor cell of the hematopoietic system, a tumor cell of the breast, a tumor cell of the ovary, a tumor cell of the colon, a tumor cell of the lymph nodes, a tumor cell of the bladder, a tumor cell of the prostate gland, a tumor cell of the stomach, or a tumor cell of the esophagus. The method may be carried out in vitro. The method may be carried out in vivo, for example, in a mammal having a tumor of the pancreas, lung, head and neck, kidney, hematopoietic system, breast, ovary, colon, lymph nodes, bladder, prostate gland, stomach, or esophagus.

BRIEF DESCRIPTION OF THE DRAWINGS

FIG. 1A shows the viability of PANC1 cells treated with or without gemcitabine (10 nM for 24 h) followed by the addition of indicated compounds for a further 48 h. FIG. 1B shows the viability of PANC1 cells treated with increasing concentrations of gemcitabine (24 h) before the addition of UCN-01 (100 nM), sunitinib (1000 nM) or bosutinib-I (1000 nM) for a further 48 h.

FIG. 3A shows a time-lapse video-microscopy of PANC1 cells treated with gemcitabine (50 nM for 24 h) before the addition of either UCN-01 (100 nM) or indicated compounds (all at 1000 nM). Shown are the examples of the fates of single cells from control, gemcitabine treated, or gemcitabine+checkpoint over-ride (both UCN-01 and Bosutinib-I) cells. FIG. 3B shows the quantification of the percentage of cells that undergo checkpoint over-ride (% of mitotic cells) after the addition of kinase inhibitors.

FIG. 5A shows the results from a panel of 300 recombinant human protein kinases tested with a panel of kinase inhibitors. The number and percentage of kinases whose in vitro activities were inhibited by more than 50% for the indicated compounds are shown. FIG. 5B shows an inhibitory profile of inhibitors against selected kinases. Those kinases inhibited by greater than 50% are shown in bold.

DETAILED DESCRIPTION OF THE INVENTION

Figure 1A:
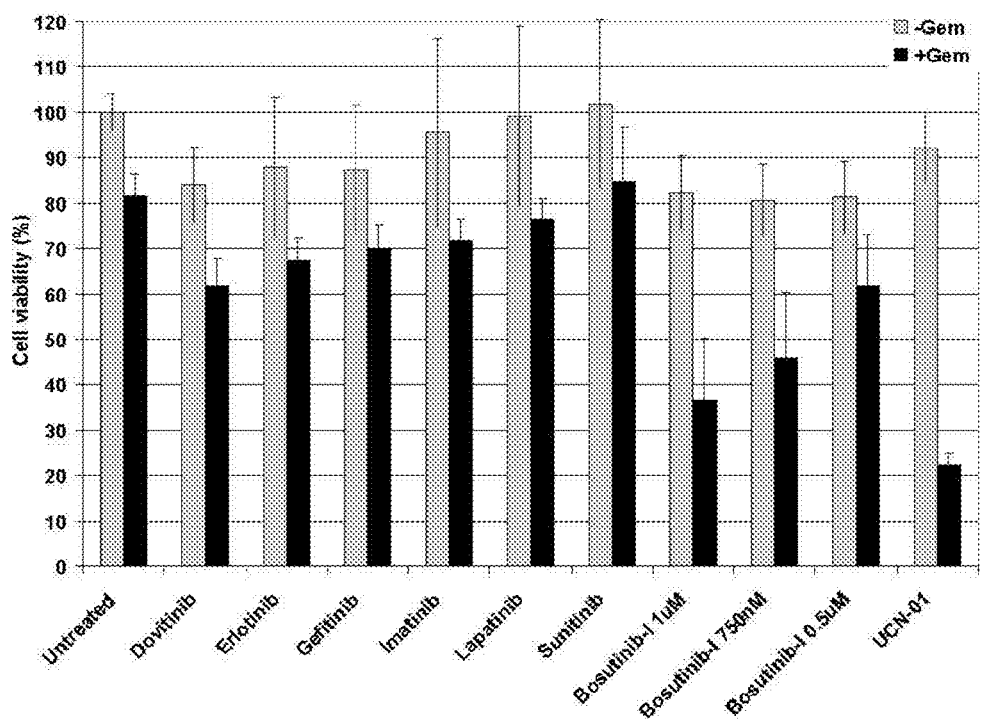
FIGS. 1A and 1B show Bosutinib-I (isomer, Formula II) sensitizes PANC1 cells to gemcitabine.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The term "about" as used herein encompasses variations of plus or minus 25%, 20%, 15%, 10%, 5%, 1%, 0.5%, 0.25%, or 0.1% from the specified value.

Bosutinib (2,4-dichloro-5-methoxyaniline) (authentic bosutinib) comprises a compound having Formula I, and all pharmaceutically acceptable salts thereof. Formula I:

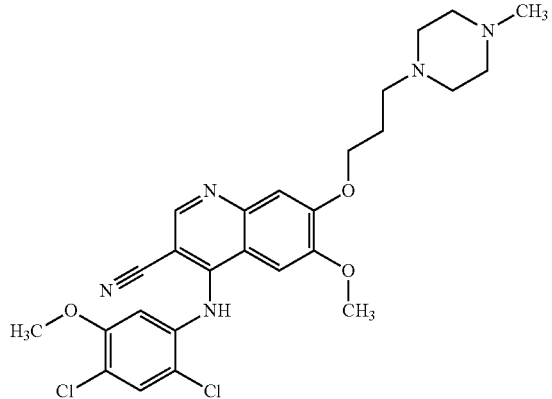

Bosutinib-I (Bos-I or the bosutinib isomer) is an isomer of bosutinib (3,5-dichloro-4-methoxyaniline), and comprises a compound having Formula II, and all pharmaceutically acceptable salts thereof. Formula II:

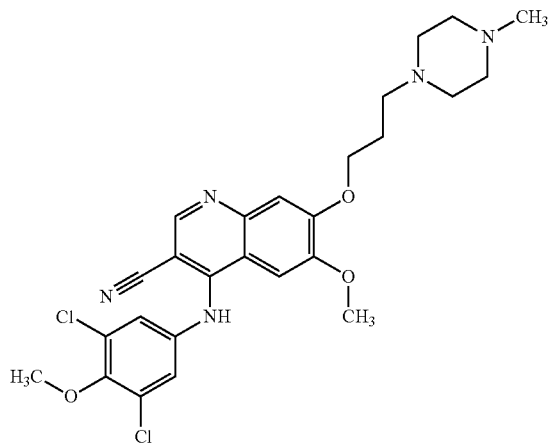

Gemcitabine comprises a compound having Formula III, and all pharmaceutically acceptable salts thereof. Formula III:

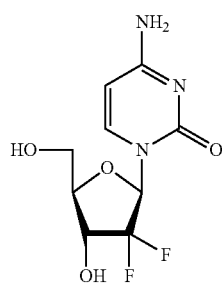 [SMILES: Nc1ccn([C@@H]2O[C@H](CO)[C@H](O)C2(F)F)c(=O)n1]

Novel isomers of bosutinib are provided, and comprise a compound having Formula IV, and all pharmaceutically acceptable salts thereof. Formula IV:

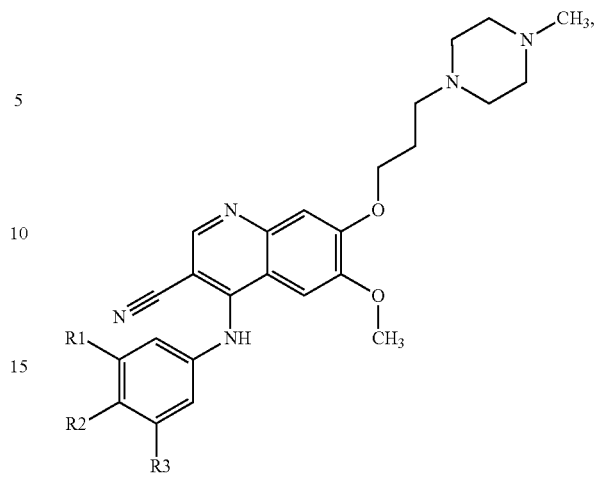

wherein each of $R_1$ and $R_3$ is independently selected from the group consisting of F, Br, and I, and wherein $R_2$ is selected from the group consisting of H and N.

Pharmaceutically acceptable salts of Formula I, Formula II, Formula III, or Formula IV may be acid or base salts. Non-limiting examples of pharmaceutically acceptable salts include sulfates, methosulfates, methanesulfates, pyrosulfates, bisulfates, sulfites, bisulfites, nitrates, besylates, phosphates, monohydrogenphosphates, dihydrogenphosphates, metaphosphates, pyrophosphates, chlorides, bromides, iodides, fluorides, acetates, propionates, decanoates, caprylates, acrylates, formates, isobutyrates, caproates, heptanoates, propiolates, oxalates, malonates, succinates, suberates, sebacates, fumarates, maleates, dioates, benzoates, chlorobenzoates, methylbenzoates, dinitromenzoates, hydroxybenzoates, methoxybenzoates, phthalates, sulfonates, toluenesulfonates, xylenesulfonates, pheylacetates, phenylpropionates, phenylbutyrates, citrates, lactates, γ-hydroxybutyrates, glycollates, tartrates, methanesulfonates, propanesulfonates, mandelates, and other salts customarily used or otherwise U.S. FDA-approved.

Inhibiting or interfering includes reducing, decreasing, blocking, preventing, delaying, inactivating, desensitizing, stopping, knocking down (e.g., knockdown), and/or down-regulating the biologic activity or expression of a molecule or pathway of interest. By way of example, but not of limitation, inhibiting the biologic activity of a kinase may include inhibiting the ability of the kinase to phosphorylate a substrate, whether or not the substrate is a normal or off target substrate.

It has been observed in accordance with the invention that the bosutinib isomer (Formula II) significantly reduces the viability of tumor cells in which DNA has been damaged by gemcitabine treatment. It was further observed that while the bosutinib isomer of Formula II sensitized tumor cells to gemcitabine at lower concentrations, authentic bosutinib (Formula I) required higher concentrations to sensitize tumor cells to gemcitabine, but nevertheless could equal or substantially approximate the level of sensitization achieved by the isomer when used at the higher concentrations. It is believed that bosutinib, including its isomer, sensitized the cells to DNA-damage-induced cell death by inhibiting kinases that mediate the DNA damage checkpoint pathway, thereby allowing the cells to override the DNA damage checkpoint and continue the cell cycle, beginning mitosis with lethal levels and/or types of DNA damage in place. It is believed that both authentic bosutinib (Formula I) and the bosutinib isomer (Formula II) target one or more of Chk1 kinase and Wee1 kinase. Accordingly, the invention features methods for enhancing the sensitivity of cancer cells to DNA damage, for example, for reducing the viability of cancer cells in which DNA has been damaged, and for treating tumors accordingly. In general, the methods comprise combining the induction of DNA damage with inhibition of the kinases Chk1 and/or Wee1 by authentic bosutinib and the bosutinib isomer, bosutinib-I or a new bosutinib isomer of Formula IV. Any of the methods of the invention may be carried out in vivo, in vitro, or in situ.

In some aspects, the invention provides methods for inhibiting DNA damage-induced cell cycle arrest in a tumor cell. In general, the methods contacting a cell in which DNA has been damaged with an amount of bosutinib (Formula I), a bosutinib isomer of Formula II, a bosutinib isomer of Formula IV, or a pharmaceutically acceptable salt thereof, effective to inhibit one or more kinases, such as Chk1 and Wee1 kinases, that are constituents of the DNA damage checkpoint of the cell cycle. Preferably, the DNA damage checkpoint comprises either the S phase or the G2 checkpoint of the cell cycle. Of note, the DNA damage checkpoint may vary according to the DNA-damaging agent or process. For example, gemcitabine arrests cells in the S phase of the cell cycle, and doxorubicin arrests cells in G2. The bosutinib (Formula I) or bosutinib isomer (Formula II or Formula IV) may be comprised within a composition comprising a pharmaceutically acceptable carrier. An effective amount of bosutinib (Formula I) may be higher than an effective amount of bosutinib isomer (Formula II or Formula IV). In some aspects, an effective amount of bosutinib (Formula I) is at least about 2.5-fold higher, or at least about 5-fold higher than an effective amount of bosutinib isomer (Formula II or Formula IV).

The methods may comprise damaging DNA in the cell. Damage to DNA may be induced before the cell is contacted with bosutinib (Formula I) or the bosutinib isomer, substantially at the same time the cell is contacted with bosutinib or the bosutinib isomer (Formula II or Formula IV), or after the cell is contacted with bosutinib or the bosutinib isomer (Formula II or Formula IV). The period of time between inducing DNA damage and contacting the cell with bosutinib or the bosutinib isomer may vary according to the needs of the investigator or medical practitioner, and the period of time may be measured in seconds, minutes, hours, or even days.

In some preferred aspects, authentic bosutinib of Formula I is used, and the kinase that is inhibited by the bosutinib isomer of Formula II is Chk1, Wee1, or both Chk1 and Wee1. In some preferred aspects, the bosutinib isomer of Formula II is used, and the kinase that is inhibited by the bosutinib isomer of Formula II is Chk1, Wee1, or both Chk1 and Wee1. In some alternative aspects, the bosutinib isomer of Formula IV is used, and the kinase that is inhibited by the bosutinib isomer of Formula IV is Chk1, Wee1, or both Chk1 and Wee1. It is preferred that inhibiting Chk1 and/or Wee1 with bosutinib (Formula I) or the bosutinib isomer (Formula II or Formula IV), or pharmaceutically acceptable salt thereof inhibits the arrest of cell cycle progression in the cell, thereby allowing the cell to progress through the S phase or G2 phase, and ultimately into the M phase of the cell cycle.

Progression of the cell cycle preferably causes or enhances cell death that stems directly or indirectly from the DNA damage. The level of cell death, for example, within a tumor in vivo or within a tumor cell culture, is higher for cells contacted with bosutinib (Formula I) or the bosutinib isomer (Formula II or Formula IV) relative to the level of cell death in cells of the same type (e.g., cells in the same tumor, or cells in a parallel cell culture) that were not contacted with bosutinib (Formula I) or the bosutinib isomer (Formula II or Formula IV).

The methods may be used to enhance the sensitivity of any tumor cell to DNA damage and DNA damage-induced cell death. For example, the tumor cell may be a tumor cell of the pancreas, a tumor cell of the head and neck, a tumor cell of the lung, a tumor cell of the kidney, a tumor cell of the breast, a tumor cell of the colon, a tumor cell of the ovary, a tumor cell of a lymph node, a tumor cell of the bladder, a tumor cell of the prostate gland, a tumor cell of the stomach, a tumor cell of the esophagus, or a tumor cell of the hematopoietic system, including a leukocyte tumor such as chronic myelogenous leukemia (CML). A tumor of the pancreas is a preferred target. A tumor of the hematopoietic system is another preferred target, including chronic myelogenous leukemia. The tumor cell may be from any organism, including mammals such as farm animals (e.g., horse, cow, sheep, pig), laboratory animals (e.g., mouse, rat, rabbit), companion animals (e.g., dog, cat), and non-human primates (e.g., new world monkey and old world monkey). In preferred aspects, the tumor cell is a human tumor cell.

DNA damage may be induced according to any suitable technique for inducing DNA damage. For example, damaging DNA may comprise irradiating the cell, or may comprise contacting the cell with an effective amount of an agent that induces DNA damage. Combinations of radiation and DNA-damaging agents may be used, as well, combinations of different DNA damaging agents may be used. Damaging DNA in a tumor cell may comprise exposing the tumor cell to an amount of radiation sufficient to damage DNA. The radiation may comprise ultraviolet radiation, ionizing radiation or may comprise x-radiation (x-ray).

Damaging DNA in a tumor cell may comprise contacting the cell with an effective amount of an agent that damages DNA, or at least inhibits repair of DNA damage. The agent may comprise an antineoplastic alkylating agent, for example, a nitrogen mustard agent, chlorambucil, melphelan, or methyl methanesulfonate; a nitrosourea agent; an alkyl sulfonate agent; a triazine agent; or an ethylenimine agent. Bendamustine is one example of an alkylating agent. The agent may comprise an antineoplastic intercalating agent, for example, a platinum agent such as cisplatin, carboplatin, or oxaliplatin. The agent may comprise a topoisomerase I inhibitor or a topoisomerase II inhibitor such as doxorubicin or etoposide. The agent may comprise a pyrimidine analog, for example, a fluoruracil or gemcitabine. Gemcitabine is highly preferred.

In some detailed aspects, the invention provides methods for enhancing the sensitivity of a tumor cell to gemcitabine, for example, reducing the viability of cells contacted with gemcitabine. The methods may comprise contacting the cell with an amount of gemcitabine, or pharmaceutically acceptable salt thereof, effective to induce DNA damage in the tumor cell, and contacting the cell with an amount of bosutinib (Formula I), a bosutinib isomer of Formula II, a bosutinib isomer of Formula IV, or a pharmaceutically acceptable salt thereof, effective to inhibit one or more kinases, such as Chk1 or Wee1 kinases, that are constituents of the DNA damage checkpoint of the cell cycle. In some preferred aspects, authentic bosutinib of Formula I is used, and the kinase that is inhibited by bosutinib of Formula I is Chk1, Wee1, or both Chk1 and Wee1. In highly preferred aspects, the bosutinib isomer of Formula II is used, and the kinase that is inhibited by the bosutinib isomer of Formula II is Chk1, Wee1, or both Chk1 and Wee1. In some preferred aspects, the bosutinib isomer of Formula IV is used, and the kinase that is inhibited by the bosutinib isomer of Formula IV is Chk1, Wee1, or both Chk1 and Wee1. The bosutinib (Formula I), the bosutinib isomer (Formula II or Formula IV), and/or the gemcitabine may be comprised within a composition comprising a pharmaceutically acceptable carrier.

It is preferred that inhibiting Chk1 and/or Wee1 with authentic bosutinib or the bosutinib isomer or pharmaceutically acceptable salt thereof inhibits the arrest of cell cycle progression in the cell, thereby allowing the cell to progress through the S phase or G2 phase, and ultimately into the M phase of the cell cycle. Progression of the cell cycle preferably causes or enhances cell death that stems directly or indirectly from DNA damage caused by gemcitabine. The level of cell death, for example, within a tumor in vivo or within a tumor cell culture, is higher for cells contacted with bosutinib (Formula I) or the bosutinib isomer (Formula II or Formula IV) relative to the level of cell death in cells of the same type (e.g., cells in the same tumor, or cells in a parallel cell culture) that were not contacted with bosutinib or the bosutinib isomer (Formula II or Formula IV), for example, cells that were contacted only with gemcitabine.

The methods are suitable for enhancing the sensitivity of any tumor cell to gemcitabine. The sensitivity may be enhanced such that lesser amounts of gemcitabine may be used to achieve cell death. It is believed that inhibition of the cell cycle DNA damage checkpoint (e.g., S phase or G2 checkpoint), for example, by inhibiting kinase constituents of the DNA damage checkpoint pathway such as Chk1 and/or Wee1 may allow the use of lower doses (e.g., sub-therapeutic doses) of gemcitabine. Use of lower doses of gemcitabine may thus reduce the toxicity of gemcitabine in a subject, and thereby allow gemcitabine to be used on tumor cells that would not be sensitive to low doses of gemcitabine in the absence of the inhibition of the DNA damage checkpoint pathway. The tumor cell may be a tumor cell of the pancreas, lung, head and neck, kidney, hematopoietic system, breast, ovary, colon, lymph nodes, bladder, prostate gland, stomach, or esophagus. Pancreatic tumor cells and leukemia cells are preferred.

In some aspects, the bosutinib (Formula I) or bosutinib isomer (Formula II or Formula IV) reduces the $LC_{50}$ of gemcitabine to less than about 20 nM. In some aspects, the bosutinib (Formula I) or bosutinib isomer (Formula II or Formula IV) reduces the $LC_{50}$ of gemcitabine to less than about 15 nM. In some aspects, the bosutinib (Formula I) or bosutinib isomer (Formula II or Formula IV) reduces the $LC_{50}$ of gemcitabine to less than about 10 nM. In some aspects, the bosutinib (Formula I) or bosutinib isomer (Formula II or Formula IV) reduces the $LC_{50}$ of gemcitabine to less than about 5 nM. In some aspects, the bosutinib (Formula I) or bosutinib isomer (Formula II or Formula IV) reduces the $LC_{50}$ of gemcitabine to about 3 nM or less. In some aspects, the bosutinib (Formula I) or bosutinib isomer (Formula II or Formula IV) reduces the $LC_{50}$ of gemcitabine to about 1 nM or less.

In any of the methods described in this specification, the bosutinib (Formula I), bosutinib isomer (Formula II or Formula IV), DNA-damaging agent (e.g., gemcitabine), or pharmaceutically acceptable salt of these agents, may be formulated as a composition, for example, with a carrier. The carrier is preferably a pharmaceutically acceptable carrier. Acceptable carriers include any that do not interfere with the biological activity of the bosutinib, bosutinib isomer (Formula II or Formula IV), or DNA-damaging agent, and preferably is not toxic to the subject to which it is administered.

The carrier may be an aqueous solution, such as water, saline, or alcohol, or a physiologically compatible buffer, such as Hanks's solution, Ringer's solution, or physiological saline buffer. The carrier may contain formulatory agents, such as suspending, stabilizing and/or dispersing agents. The carrier may include a nonaqueous vehicle such as a nonpolar alcohol or oil, including plant or vegetable-derived oils such as olive oil, cottonseed oil, corn oil, canola oil, sesame oil, and other non-toxic oils.

The compositions may also be formulated in sustained release vehicles or depot preparations. For example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes, micelles, and emulsions are well-known examples of such delivery vehicles.

An effective amount may comprise from about 0.01 µM to about 1 mM of the agent, for example bosutinib (Formula I) or pharmaceutically acceptable salt thereof, or bosutinib isomer (Formula II or Formula IV) or pharmaceutically acceptable salt thereof, or DNA-damaging agent, a non-limiting example of the latter being gemcitabine. An effective amount may comprise from about 0.1 µM to about 500 µM. An effective amount may comprise from about 0.1 µM to about 100 µM. An effective amount may comprise from about 0.1 µM to about 50 µM. An effective amount may comprise from about 0.1 µM to about 5 µM. An effective amount may comprise from about 0.1 µM to about 3 µM. An effective amount may comprise from about 0.1 µM to about 1 µM. An effective amount may comprise from about 0.1 µM to about 2.5 µM. An effective amount may comprise from about 1 µM to about 2.5 µM. An effective amount may comprise from about 1 µM to about 5 µM. An effective amount may comprise from about 2.5 µM to about 5 µM. An effective amount may comprise from about 0.5 µM to about 1 µM. An effective amount may comprise from about 0.5 µM to about 1.5 µM. An effective amount may comprise from about 0.6 µM to about 0.8 µM. An effective amount may comprise at least about 0.75 µM. An effective amount may comprise at least about 1 µM. An effective amount may comprise at least about 2 µM. An effective amount may comprise at least about 2.5 µM. An effective amount may comprise at least about 4 µM. An effective amount may comprise at least about 5 µM. The µM concentration may be determined according to any suitable method, and may constitute the concentration in the blood of a subject, or in the macro-environment of the tumor, or in the micro-environment of the tumor, or in the micro-environment of cells of the tumor. It is to be understood, however, that the concentration may vary depending on the cell type, tumor type, tumor location, tumor size, physical characteristics of the subject (species, age, height, weight, gender, among others).

The invention also features methods for treating malignancies in a subject in need thereof. The malignancy may include, but is not limited to a malignancy of the pancreas, a malignancy of the head and neck, a malignancy of the lung, a malignancy of the hematopoietic system (e.g., a leukemia), a malignancy of the kidney, a malignancy of the bladder, a malignancy of the prostate gland, a malignancy of the colon, a malignancy of the breast, a malignancy of the ovary, a malignancy of the lymph nodes, a malignancy of the stomach, or a malignancy of the esophagus. Preferred methods are those for treating a malignancy of the pancreas. The malignancy may be a malignancy that is not sensitive to low doses of gemcitabine in the absence of the inhibition of the DNA damage checkpoint pathway, for example, inhibition caused by bosutinib (Formula I) or the bosutinib isomer (Formula II or Formula IV). The subject may be a mammal such as a farm animal (e.g., horse, cow, sheep, pig), laboratory animal (e.g., mouse, rat, rabbit), companion animal (e.g., dog, cat), or non-human primate (e.g., new world monkey and old world monkey). In preferred aspects, the subject is a human being.

In general, a method for treating a malignancy of the pancreas, lung, head and neck, hematopoietic system, kidney, bladder, prostate gland, colon, breast, ovary, lymph nodes, stomach, or esophagus, among others, comprises damaging DNA in a cell of the malignancy and administering to the subject an amount of bosutinib (Formula I), a bosutinib isomer of Formula II, a bosutinib isomer of Formula IV, or a pharmaceutically acceptable salt thereof, effective to inhibit one or more kinases, such as Chk1 or Wee1 kinases, that are constituents of the DNA damage checkpoint of the cell cycle in the cell of the malignancy. Chk1, Wee1, or a combination of Chk1 and Wee1 are preferably inhibited. The bosutinib (Formula I) or bosutinib isomer (Formula II or Formula IV) may be comprised within a composition comprising a pharmaceutically acceptable carrier.

Damaging DNA in a cell of the malignancy may comprise irradiating the malignancy in the subject according to any suitable technique for irradiating a malignancy. Damaging DNA in a cell of the malignancy may comprise administering to the subject an amount of a DNA damaging agent effective to damage DNA in the cell. The DNA-damaging agent may be administered systemically, or may be administered locally or proximally to the site of the malignancy. The agent may be specifically targeted to the malignancy. The agent may comprise an antineoplastic alkylating agent, for example, a nitrogen mustard agent, chlorambucil, melphelan, or methyl methanesulfonate; a nitrosourea agent; an alkyl sulfonate agent; a triazine agent; or an ethylenimine agent. Bendamustine is one example of an alkylating agent. The agent may comprise an antineoplastic intercalating agent, for example, a platinum agent such as cisplatin, carboplatin, or oxaliplatin. The agent may comprise a topoisomerase I inhibitor or a topoisomerase II inhibitor such as doxorubicin or etoposide. The agent may comprise a pyrimidine analog, for example, a fluoruracil or gemcitabine. Gemcitabine is highly preferred. The DNA damaging agent may be comprised in a pharmaceutically acceptable carrier.

The invention also features kits. The kits may be used, for example, to practice any of the methods described or exemplified herein. In some aspects, a kit comprises a DNA damaging agent, and bosutinib (Formula I) or a pharmaceutically acceptable salt thereof, or the bosutinib isomer of Formula II or a pharmaceutically acceptable salt thereof, or the bosutinib isomer of Formula IV or a pharmaceutically acceptable salt thereof, and instructions for using the kit in method which may be any of the methods described or exemplified herein. For example, the instructions may be for using the kit in a method for inhibiting DNA damage-induced cell cycle arrest in a tumor cell. The instructions may be for using the kit in a method for enhancing the sensitivity of a tumor cell to gemcitabine. The instructions may be for using the kit in a method for treating a malignancy of the pancreas, lung, head and neck, hematopoietic system, kidney, bladder, prostate gland, colon, breast, ovary, lymph nodes, stomach, or esophagus in a subject in need thereof.

In the kits, the DNA damaging agent may comprise an antineoplastic alkylating agent, for example, a nitrogen mustard agent, chlorambucil, melphelan, or methyl methanesulfonate; a nitrosourea agent; an alkyl sulfonate agent; a triazine agent; or an ethylenimine agent. Bendamustine is one example of an alkylating agent. The agent may comprise an antineoplastic intercalating agent, for example, a platinum agent such as cisplatin, carboplatin, or oxaliplatin. The agent may comprise a topoisomerase I inhibitor or a topoisomerase II inhibitor such as doxorubicin or etoposide. The agent may comprise a pyrimidine analog, for example, a fluoruracil or gemcitabine. In preferred kits, the DNA damaging agent is gemcitabine.

The DNA damaging agent, bosutinib (Formula I), or bosutinib isomer (Formula II or Formula IV), or a pharmaceutically acceptable salt thereof, may be comprised in a composition with a pharmaceutically acceptable carrier. In some alternative aspects, the kits further comprise a pharmaceutically acceptable carrier for one or more of the DNA damaging agent, bosutinib, or bosutinib isomer (Formula II or Formula IV). The kits may comprise instructions for preparing a composition of the DNA damaging agent, bosutinib, or bosutinib isomer (Formula II or Formula IV) and the carrier.

The DNA damaging agent, bosutinib, or bosutinib isomer (Formula II or Formula IV) may be present in the kit in pre-measured effective amounts (e.g., effective for inhibiting Chk1, Wee1, or both, or effective for sensitizing tumor cells to DNA damage). In preferred aspects, the instructions for using the kit provide additional instructions for determining an effective amount for the particular application in which the kit will be used, for example, for determining the effective amount that may be administered to a subject to induce DNA damage and/or to inhibit one or more kinases, such as Chk1 or Wee1 kinases, that are constituents of the DNA damage checkpoint of the cell cycle in the cell of the malignancy. Chk1, Wee1, or a combination of Chk1 and Wee1 are preferably inhibited.

The following examples are provided to describe the invention in greater detail. They are intended to illustrate, not to limit, the invention.

Example 1

The Bosutinib Isomer Inhibits DNA Damage Checkpoint Control

Kinase inhibitors are designed to bind to the conserved ATP pocket of protein kinases to inhibit catalytic activity. As such, it is believed that inhibitors are rarely specific for a single kinase, but rather, display a broad range of inhibitory activity to other kinases, generally referred to as off-target kinases. It is believed that it is possible to take advantage of the off-target effects of inhibitors and repurpose them to be used to enhance the killing of cancer cells caused by standard chemotherapeutic agents such as gemcitabine.

Identification of clinically relevant kinase inhibitors that sensitize cells to gemcitabine. In the experiments described in this Example, the general protocol was to treat pancreatic cancer cell line (Panc-1) with a dose of gemcitabine that induces DNA damage and arrests cell cycle progression. A panel of nine different clinically relevant kinase inhibitors (FIG. 1A) were added to gemcitabine treated cells, and were assessed for their ability to enhance killing of pancreatic cancer cells to gemcitabine. PANC1 cells were treated with a sub-lethal ($IC_{20}$) concentration of gemcitabine (10 nM) for 24 hours (a time and concentration sufficient to induce DNA damage and S phase arrest) and kinase inhibitors (all at 1 µM final) were added for another 48 h before cell viability was measured. UCN-01, a Chk1 inhibitor that is established as a sensitizer of gemcitabine was included as a positive control. Viability measurements are presented in FIG. 1A.

The screen identified three compounds, bosutinib, BEZ-235 and dovitinib, which significantly reduced viability of cells treated with gemcitabine. The assay was repeated with cells treated with different concentration of gemcitabine before the addition of UCN-01 (100 nM), bosutinib and sunitinib (both 1 μM). In agreement with the primary screen, both UCN-01 and bosutinib, but not sunitinib, sensitized cells to gemcitabine. FIG. 1B. Next, the amount of bosutinib used in the assay was titrated to determine the minimum effective concentration to sensitize cells to gemcitabine, and this concentration was determined to be 750 nM.

Off-target activities towards the checkpoint response pathway suggests a mechanism of action for sensitization. To investigate the mechanism of chemosensitization by bosutinib and dovitinib, a database (www.reactionbiology.com/webapps/largedata/) containing the inhibitory activities of 178 kinase inhibitors was queried against a panel of 300 recombinant human kinases. The query showed that bosutinib inhibited 84/300 kinases by more than 50%, while dovitinib inhibited 65/300. As a comparison, the Src/Abl inhibitor dasatinib inhibited 50/300 kinases. All hits were analyzed by STRING 9.0 to search for known and predicted protein-protein interactions to help elucidate signaling networks. Bosutinib retrieved a signaling node centered on the Src family kinases as well as Abl, which are the primary targets of this drug. The analysis also showed that bosutinib might target the DNA damage checkpoint pathway by inhibiting Chk1 and Wee1. The same analysis when applied to dovitinib identified the Src family kinases for an inhibitor of receptor tyrosine kinases. In addition, STRING also identified Chk1 as a target for dovitinib. When the kinase targets and signaling node of dasatinib, another Src/Abl inhibitor, were compared, no connections with Chk1 or Wee1 were identified. This suggested that gemcitabine sensitization by bosutinib was not due to inhibition of Src family or Abl kinases. Without intending to be limited to any particular theory or mechanism of action, it is believed that the mechanism of gemcitabine sensitization may be due to checkpoint override through off-target effects on Chk1 and/or Wee1 kinases.

During the course of these studies, it came to light that numerous vendors had unknowingly sold to the research community an incorrectly synthesized isomer of bosutinib (bosutinib-I, Formula II), but because it was not known that the material sold was actually an isomer, these compounds were packaged and sold as authentic bosutinib (Formula I). The two compounds differ in the arrangement of the same R groups around the aniline ring. The experiments described above, including the data reported in FIG. 1A and FIG. 1B, were conducted using the bosutinib isomer, although it was not known at the time that the isomer was used.

Once it was determined that the bosutinib compound tested was actually the isomer, follow-up studies were conducted to compare the relative kinase inhibitory profiles of authentic bosutinib (Formula I, obtained from TOCRIS) and the bosutinib isomer (Formula II, obtained from LC Labs). Using >50% inhibitory activity as a cut-off, it was determined that both compounds inhibited a common set of 71 kinases, which notably include the Src family kinases. Seventeen additional kinases were more selectively inhibited by the authentic bosutinib, while thirty additional kinases were more selectively inhibited by the bosutinib isomer. Interestingly, Chk1 and Wee1 were kinases that were more potently inhibited by the bosutinib isomer compared to the authentic bosutinib.

Figure 2:
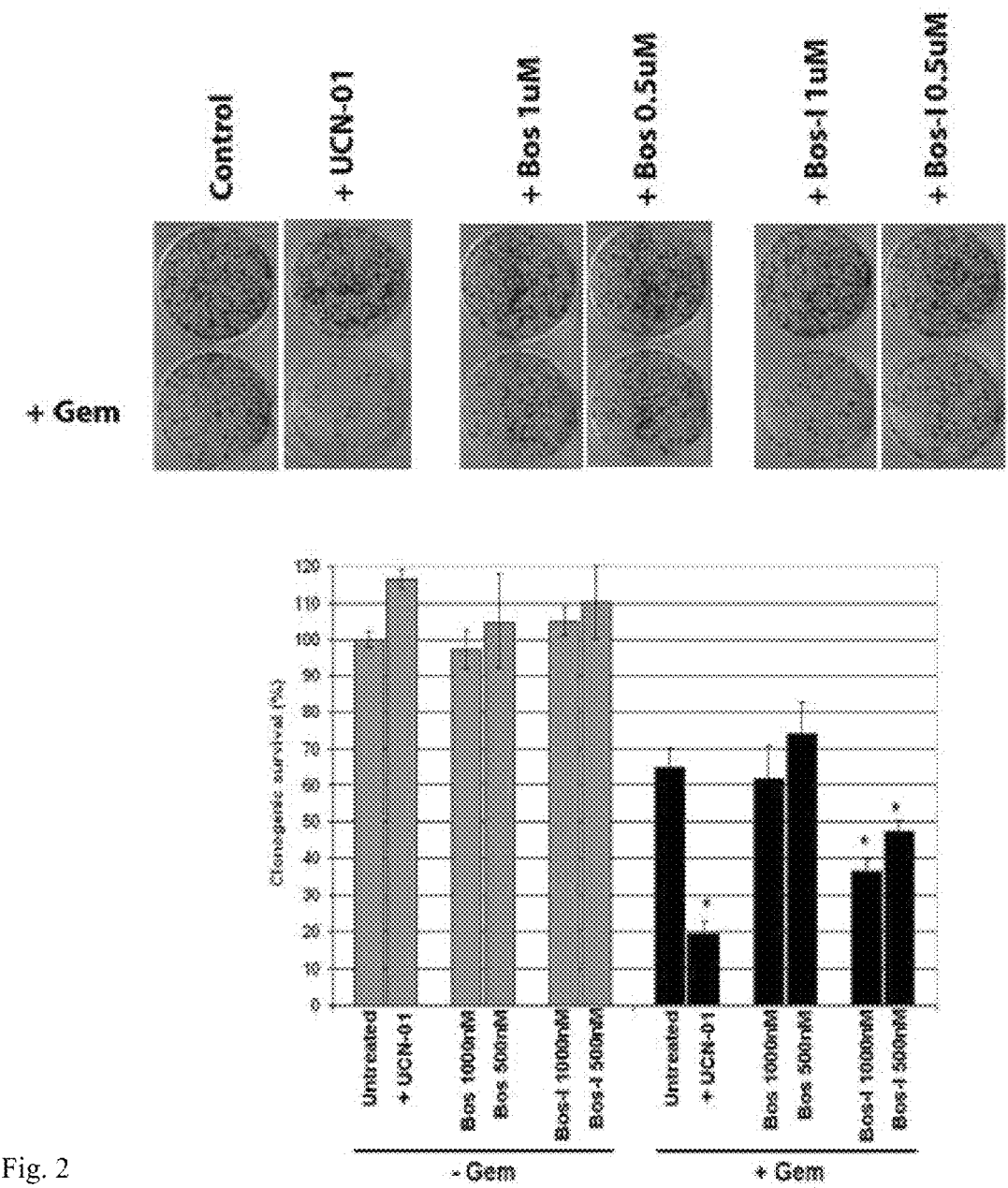
FIG. 2 shows Bosutinib-I at 1 µM (isomer, Formula II), but not bosutinib (Formula I) at low concentration (0.5 µM), sensitized cells to killing by gemcitabine in a clonogenic survival assay. PANC1 cells were treated with gemcitabine (10 nM for 24 h) followed by the addition of bosutinib or bosutinib-I (0.5 and 1.0 µM, respectively) for 3 h before all drugs were washed out. Surviving colonies were determined 10 days later.

To compare the relative potencies of the authentic bosutinib and isomer towards Chk1 and Wee1, the $IC_{50}$ values of each compound toward recombinant Src, Chk1 and Wee1 were determined. Authentic bosutinib was more potent towards Src (~5 fold), while the bosutinib isomer was more potent towards Chk1 (~6 fold) and Wee1 (~17 fold), as shown in FIG. 2 and Table 1.

TABLE 1

Comparison of authentic bosutinib and bosutinib $IC_{50}$ (mM) for Src, Chk1 and Wee 1.

|  | c-Src | Chk1 | Wee 1 |
|---|---|---|---|
| Authentic bosutinib | <1.52 × 10⁻⁹ | 7.93 × 10⁻⁷ | 6.67 × 10⁻⁷ |
| Bosutinib isomer | 7.51 × 10⁻⁹ | 1.3 × 10⁻⁷ | 3.85 × 10⁻⁸ |
| Fold difference | 4.9 | 6.1 | 17.3 |

These in vitro assays used MBP as a substrate of Wee1, so the next tests evaluated Wee1 inhibitory activity of the bosutinib isomer in kinase assays against the physiologically relevant substrate, Cdc2 (data not shown). These in vitro studies recapitulated the studies that used MBP as a substrate. It was also determined that Bos-I caused a dose-dependent inhibition of Tyr15 phosphorylation of Cdc2 in PANC1 cells treated with gemcitabine. Inhibition of Tyr15 phosphorylation was not observed for dasatnib, which is fully consistent with its in vitro kinase profile, and its inability to override the DNA damage checkpoint.

Figure 7A:
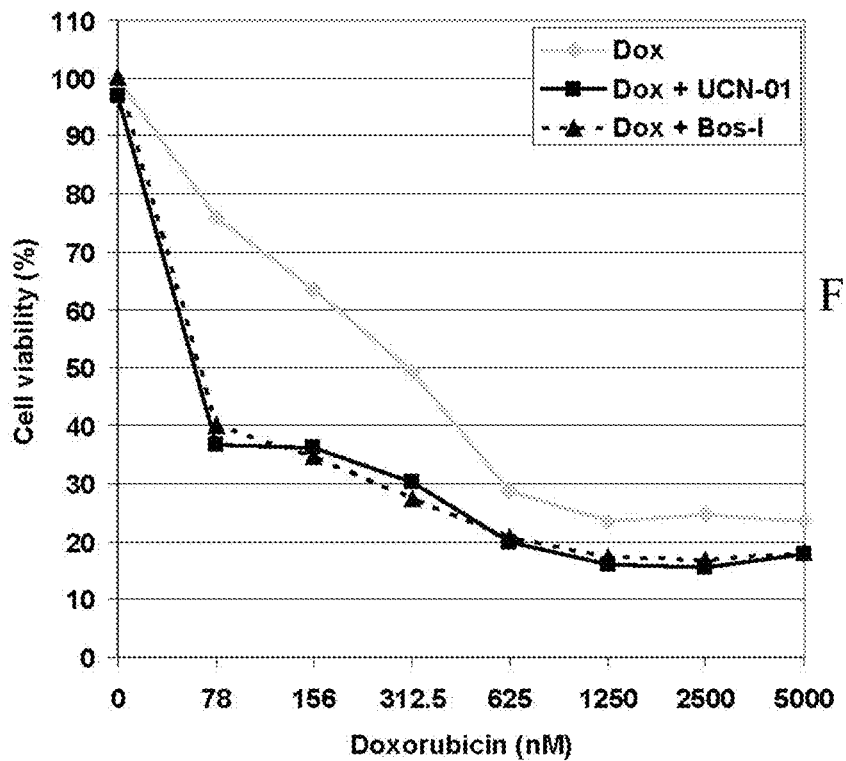
FIGS. 7A-7D show the viability of PANC1 cells treated with increasing concentrations of (FIG. 7A) doxorubicin or (FIG. 7B) cisplatin (24 h) before the addition of UCN-01 (100 nM) or Bos-I (1000 nM) for a further 48 hours. The viability of (FIG. 7C) PANC1 and (FIG. 7D) Mia-PaCa-II cells was determined following treatment with increasing concentrations of gemcitabine (24 h) before the addition of authentic bosutinib at 2.5 µM and 5 µM for an additional 48 h.
Figure 7B:
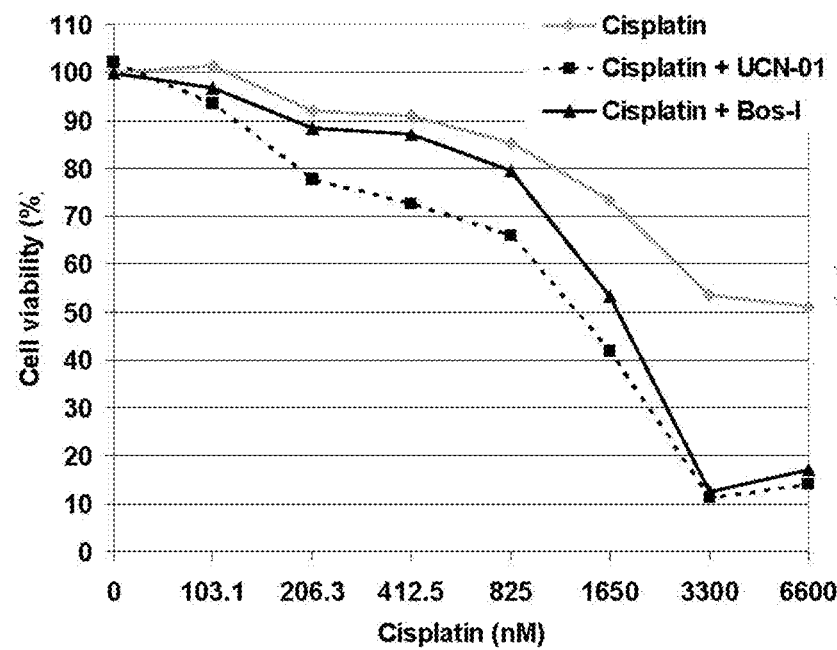
Figure 7C:
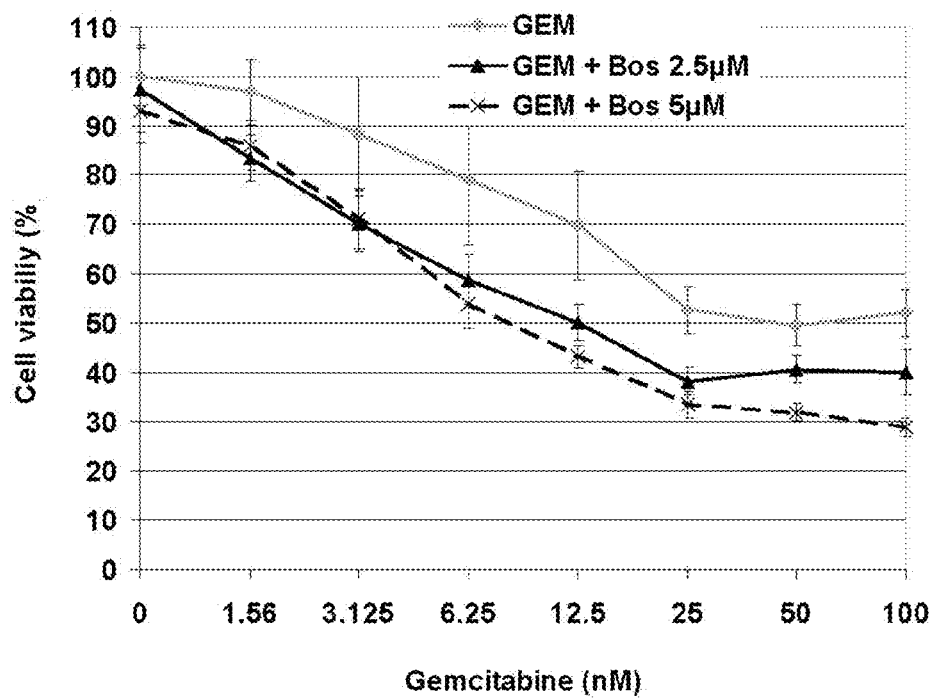
Figure 7D:
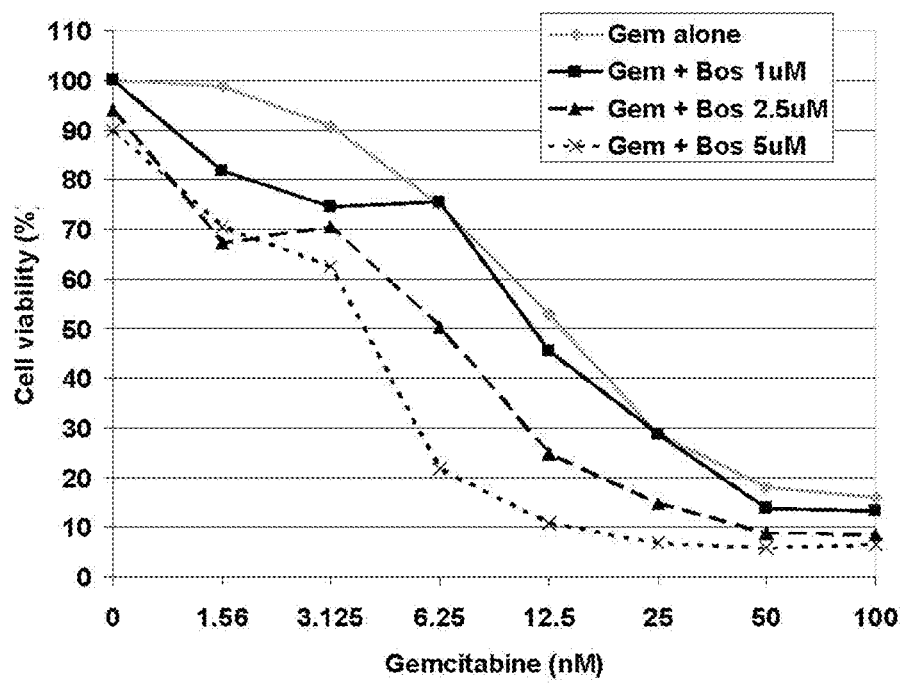

Having demonstrated a difference in the in vitro potencies towards the checkpoint proteins Chk1 and Wee1, their chemosensitization properties were next compared. When used at 1 uM, bosutinib isomer, but not the authentic bosutinib, sensitized cells to gemcitabine as determined by MTS assay and clonogenic assays. Given that the authentic bosutinib was a weaker inhibitor of Chk1 and Wee1 when compared to the isomer in vitro, it was hypothesized that increasing its concentration might cause sensitization to gemcitabine. Experiments showed that increasing the concentration of the authentic bosutinib (to 2.5 μM and 5 μM) sensitized PANC1 cells to gemcitabine (FIG. 7C and FIG. 7D). By contrast, increasing the concentration of dasatinib to 2.5 and 5 μM did not enhance killing by gemcitabine (data not shown).

Example 2

Gemcitabine Sensitization Occurs Through Bosutinib-Mediated Checkpoint Override

Figure 3A:
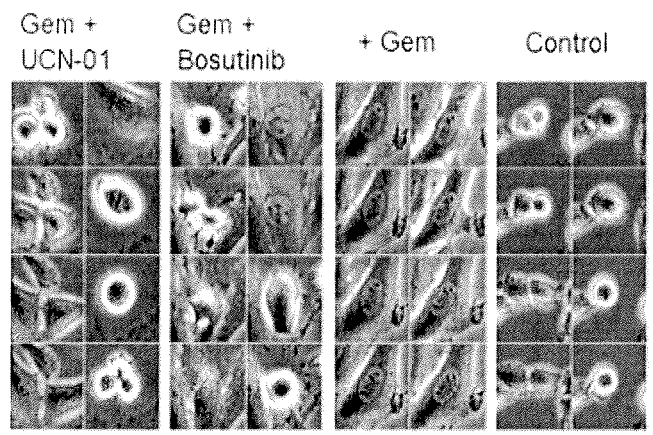
FIGS. 3A and 3B show Bosutinib-I (isomer, Formula II) causes checkpoint over-ride as evidence by premature entry into mitosis.

Time-lapse microscopy was used to directly examine the effects of bosutinib, dovitinib on Panc1 cells that were arrested by gemcitabine. PANC1 cells were treated with gemcitabine for 24 hours before the addition of kinase inhibitors (1 μM), and filming commenced thereafter. UCN-01 forced cells to prematurely enter mitosis. Of the inhibitors tested, only dovitinib and bosutinib were able to override the checkpoint and force cells into premature mitosis, as shown in FIG. 3A.

Figure 4:
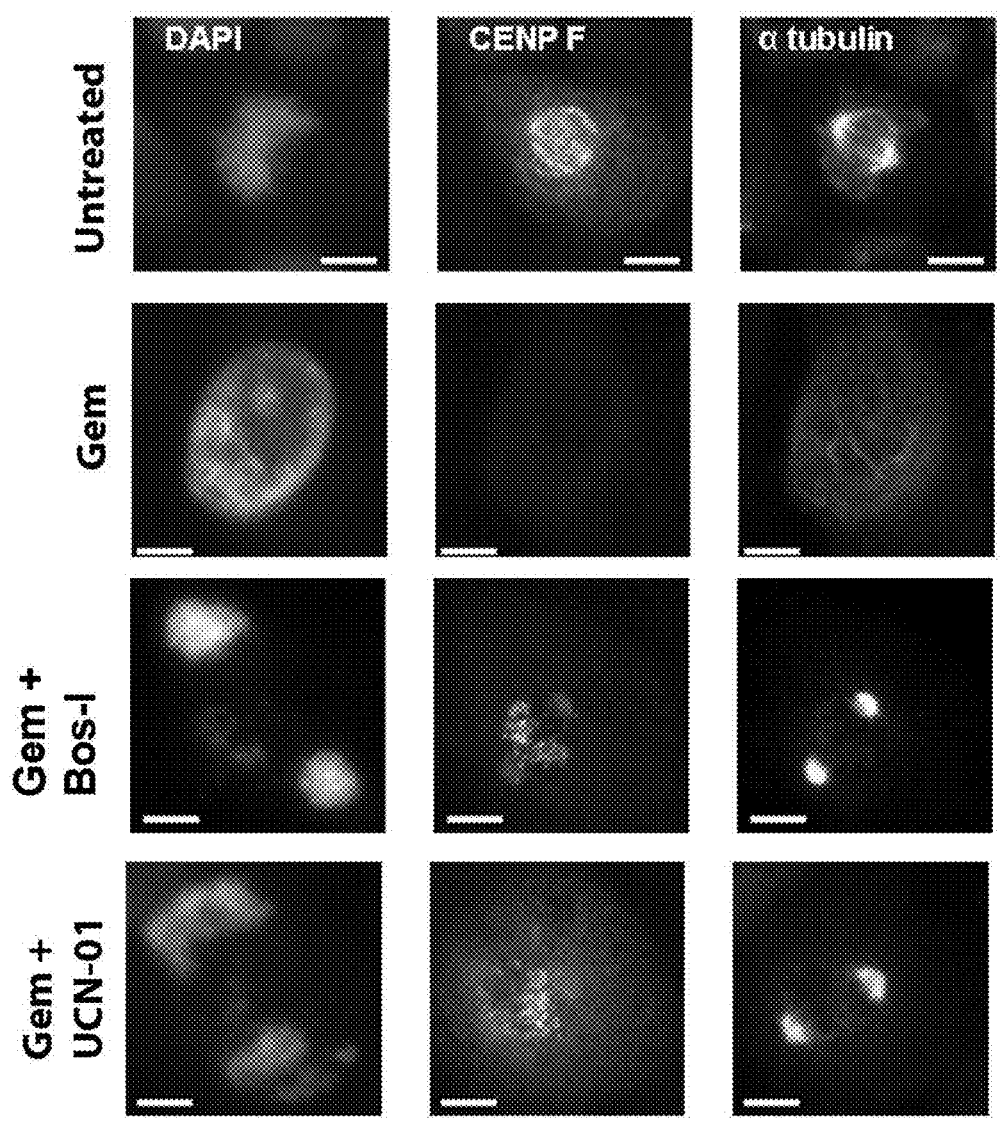
FIG. 4 shows images of immunofluorescence studies performed in cells treated with gemcitabine or gemcitabine+ UCN-01 (100 nM) or Bos-I (1000 nM). Shown are representative images of cells from each treatment. DAPI was used to stain DNA and show chromosomal integrity, CENP-F was used to demonstrate localization of kinetochores/centromeres and α-tubulin to show the mitotic spindle.

The mitotic figures of cells forced into mitosis by the newly identified sensitizers were examined to determine how they compared to checkpoint override by UCN-01. As shown in FIG. 4, control mitotic cells, chromosomes and their kinetochores were positioned at the spindle equator. When gemcitabine-arrested cells were treated with UCN-01, however, severely perturbed mitotic figures were observed. The defects include two lobes of chromatin that lie outside of the spindle, with the detached kinetochores lying within the spindle. The bosutinib isomer produced the abnormal mitotic figures from gemcitabine-arrested cells that were nearly indistinguishable from UCN-01 treatment. Taken together, these studies show that the bosutinib isomer is able to override the DNA damage checkpoint and force cells into premature mitosis.

Example 3

Checkpoint Override is Observed in Multiple Cell Lines and with Different Chemotherapeutic Agents The utility of authentic bosutinib (Formula I) and the bosutinib isomer (Formula II) was assessed by sensitizing cells to different DNA damaging drugs. When PANC1 cells were treated with the topoisomerase II inhibitor doxorubicin or the DNA cross-linking agent cisplatin, sensitization by the bosutinib isomer was observed at 1 µM of the isomer. (FIG. 7A and FIG. 7B, respectively). Sensitization to gemcitabine was observed in PANC1 cells when authentic bosutinib was used at 2.5 µM and 5 µM (FIG. 7C). In addition, Mia-PaCa-II cells were sensitized to gemcitabine with authentic bosutinib at 2.5 µM and 5 µM (FIG. 7D).

Figure 8:
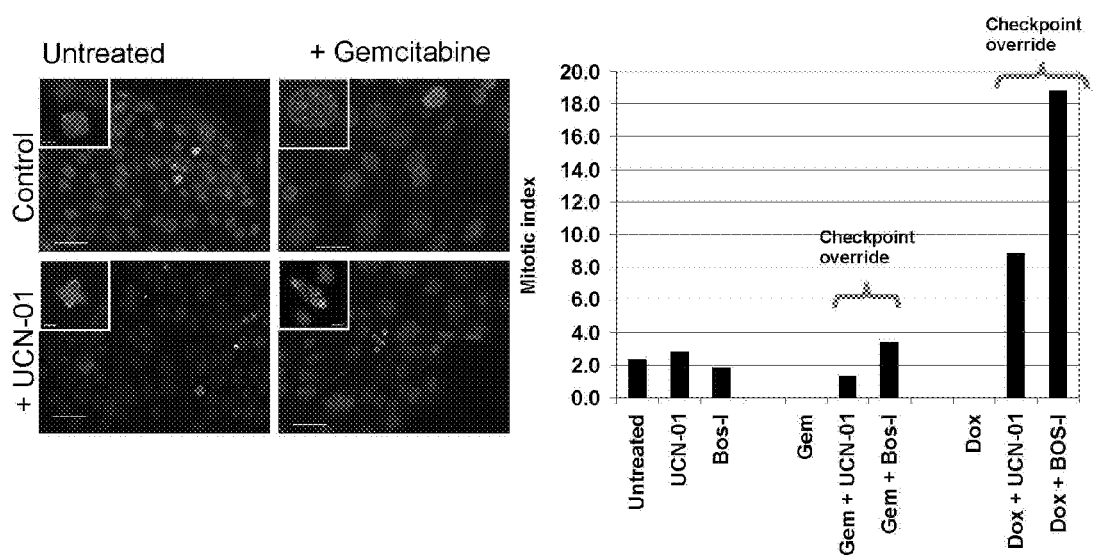
FIG. 8 shows images (left panel) from immunofluorescence analysis of a patient-derived pancreatic cancer cell line (EGF-1). Quantification of the percentage of cells that enter mitosis/override the checkpoint after treatment with either gemcitabine or doxorubicin is shown (right panel).

These observations were extended to test the effectiveness of the bosutinib isomer as a chemosensitizer in pancreatic cancer cells that were isolated from a patient. Tumor cells were isolated under an IRB-approved protocol and passaged as xenografts in mice. EGF-1 is a cell line that was derived from F1 tumors and used for in vitro studies. Using these cells, it was confirmed by immunofluorescence that the cells were able to prematurely enter mitosis after overriding checkpoint arrests imposed by either gemcitabine or doxorubicin (FIG. 8B). The defective mitotic figures were comparable with what was observed in pancreatic cancer cell lines (FIG. 4B).

Figure 9A:
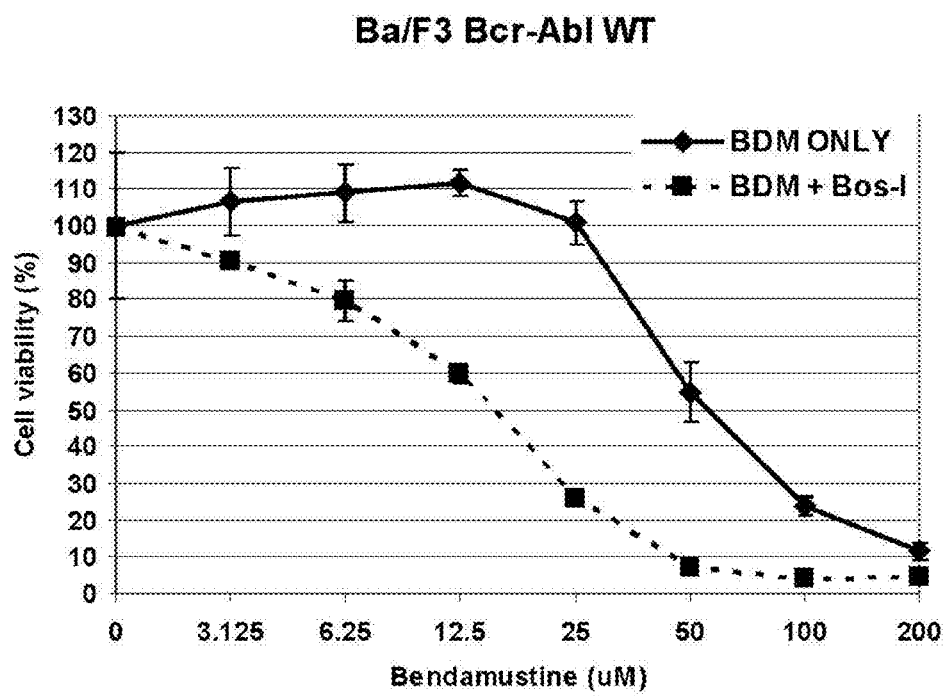
FIGS. 9A and 9B show the viability of Ba/F3 cells either expressing (FIG. 9A) the Bcr-Abl wild-type (WT) or (FIG. 9B) the Bcr-Abl mutant (T3151) kinases (lower) treated with increasing concentrations of bendamustine alone or with the addition of Bos-1 (1000 nM).
Figure 9B:
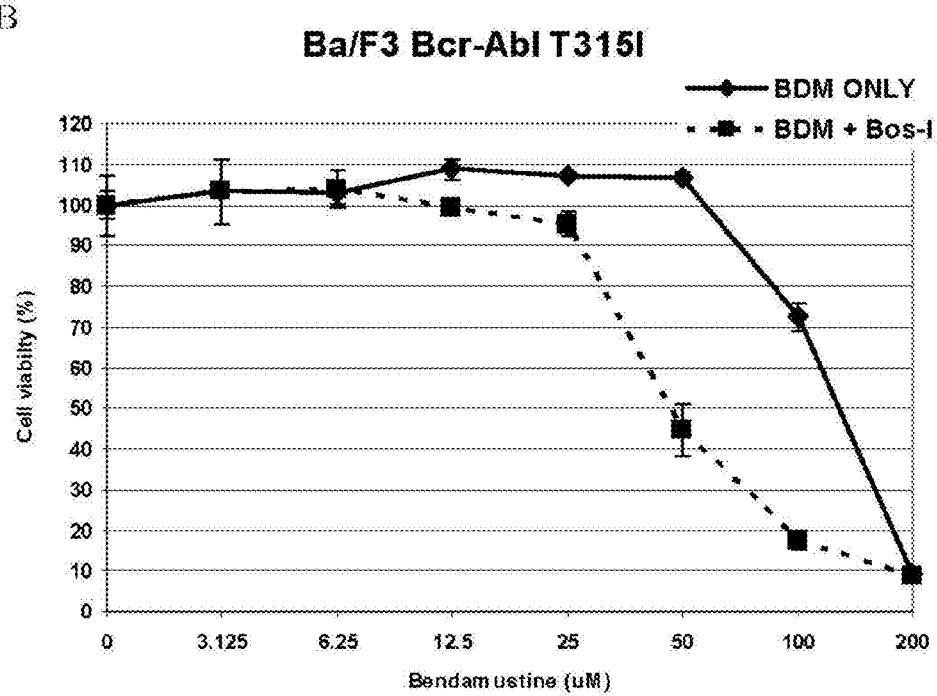

It is believed that inhibitors of Src and Abl tyrosine kinases may be effective as a single agent in the treatment of CML (Chronic myelogenous leukemia) where it contains a specific chromosome translocation that fuses the Abl kinase to the Bcr gene. Inhibitors of the Bcr/Abl fusion kinase, such as imatinib and bostunib (Formula I), are effective in the treatment of CML, but resistance (at least for imatinib) invariably occurs. Resistance to imatinib occurs most often as a result of mutations at the gatekeeper position (Threonine 315) within the Abl kinase domain. Such mutants no longer respond to inhibitors such as imatinib. The bosutinib-isomer (Formula II), when used in combination with a DNA damaging drug such as Bendamustine, enhanced killing of cells that express either the wild-type or the T315I Bcr/Abl mutant. (FIG. 9A and FIG. 9B). It is believed that the activity of Bosutinib-isomer against wild type and T315I mutant is likely mediated through its off-target effects against the DNA damage checkpoint kinases, Wee1 and Chk1. Thus, bosutinib and the bosutinib-isomer may be used in the context of chemosensitization for cases of CML whose Bcr/Abl kinase have developed resistance to inhibitors such as imatinib and bosutnib.

Figure 1B:
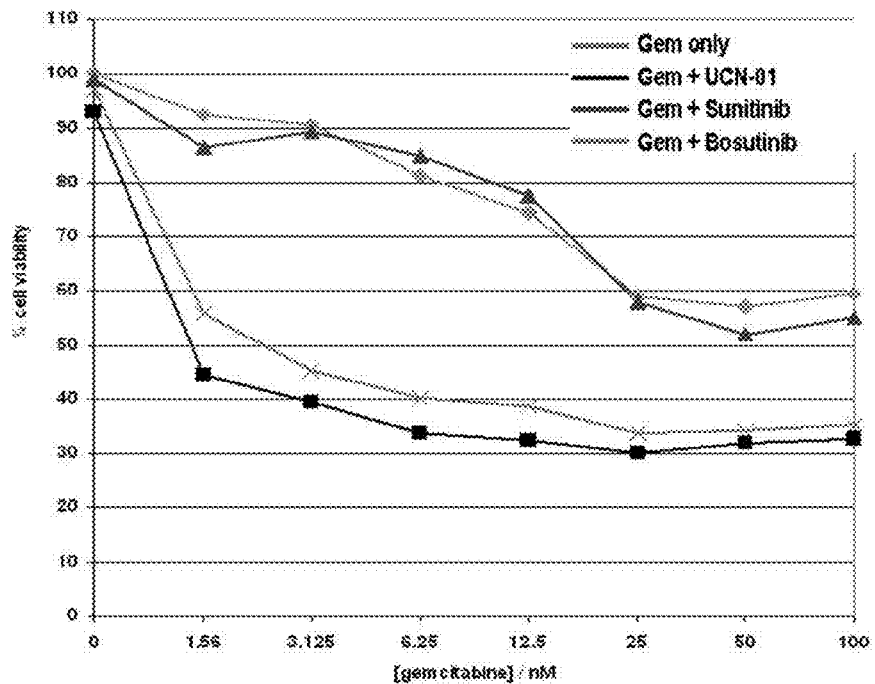

The data show that bosutinib-isomer (Formula II) reduced the viability of gemcitabine treated cells in a dose-dependent manner, and significantly diminished cell viability compared to gemcitabine treatment alone (FIG. 1A and FIG. 1B). The cell viability reduction caused by the bosutinib-isomer was similar to that observed with UCN-01, a known inhibitor of the Chk1 DNA damage checkpoint kinase, and known sensitizer of gemcitabine. The other kinase inhibitors tested did not significantly reduce the viability of the gemcitabine treated cells.

Next, the degree of gemcitabine sensitization by bosutinib-isomer (Formula II) was tested by comparing the dose-dependent killing of cells by gemcitabine in the presence of 1 µM of bosutinib isomer. As can be seen in FIG. 1B, the presence of bosutinib-isomer reduced the $LC_{50}$ of gemcitabine to ~3 nM while the $LC_{50}$ of gemcitabine alone was >30 nM. The degree of sensitization achieved with bosutinib-isomer was similar to that achieved with the addition of UCN-01. No sensitization was achieved with sunitinib, which inhibits a number of tyrosine receptor kinases including platelet-derived growth factor receptor (PDGFR) and vascular endothelial growth factor receptor (VEGFR).

It is believed that neither authentic bosutinib nor the bosutinib isomer have been previously reported to enhance killing of cancer cells by gemcitabine, and is thus may have novel indications for improving the outcome of cancer patients undergoing gemcitabine, or related chemotherapy, or other DNA damaging therapy.

The bosutinib-isomer (Formula II) is structurally related to authentic bosutinib (Formula I) (with identical empirical molecular formula $C_{26}H_{29}Cl_2N_5O_3$) and both compounds inhibit Src/Abl tyrosine kinases. The bosutinib-isomer differs in the arrangement of two chloride groups and a methoxy group within the aniline ring. Bosutinib has the designation 2,4-dichloro-5-methoxyaniline, and the isomer has the designation 3,5-dichloro-4-methoxyaniline. Comparative studies showed that authentic bosutinib does not enhance the killing of Panc 1 cells by gemcitabine when used at 1 µM (FIG. 2), e.g., the composition at which the bosutinib-isomer was shown to be effective, but does enhance their killing at higher concentrations, including at 2.5 µM or at 5 µM.

It is believed that the authentic bosutinib (Formula I) and the bosutinib-isomer (Formula II) each sensitize cells to killing by gemcitabine by inhibiting the DNA damage checkpoint pathway. Cells treated with gemcitabine, and related drugs, arrest in the S phase portion of the cell cycle because they cannot replicate their DNA. The cell cycle arrest is mediated by the DNA damage checkpoint pathway, which consists of many proteins, some of which are protein kinases such as Chk1 and Wee1. It is believed that inhibition of this checkpoint pathway prevents cells treated with gemcitabine or related drugs from arresting their cell cycle. As a consequence, the gemcitabine treated cells inappropriately progress through the cell cycle and enter mitosis to attempt to divide. Entry into mitosis with incompletely replicated DNA (genome) leads to cell death, which is how inhibitors of the DNA damage checkpoint are thought to sensitize killing of cells by drugs such as gemcitabine.

Figure 3B:
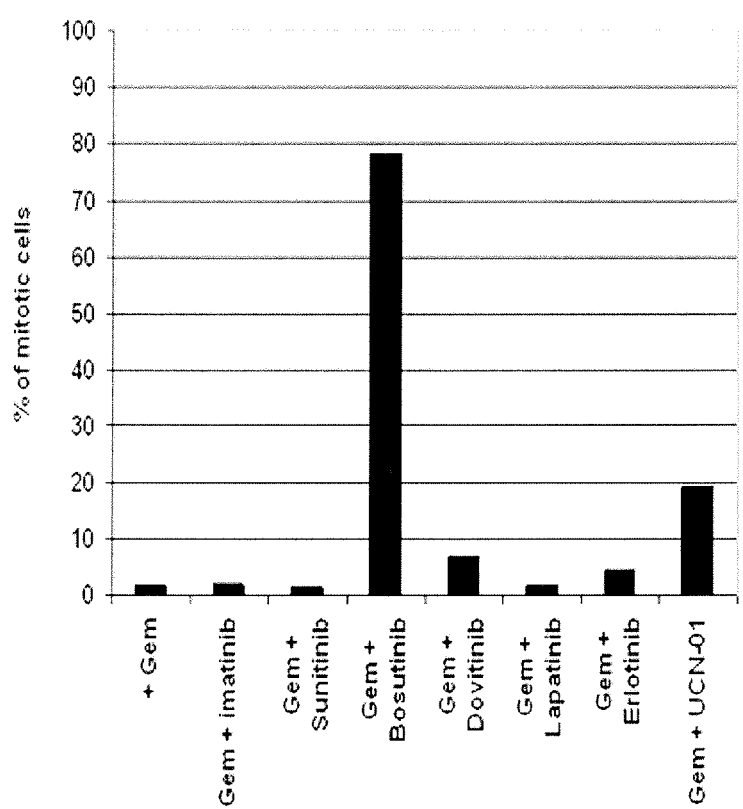

Time-lapse video microscopy was used to document the fates of cells treated with gemcitabine with and without the Chk1 inhibitor, UCN-01 (FIG. 3). When compared to gemcitabine alone, the presence of UCN-01 increased the number of cells that entered mitosis, over the course of the time-lapse experiment (24 hours). The addition of bosutinib-isomer to the gemcitabine treated cells also increased the number of mitotic cells when compared to gemcitabine treatment alone. However, the percentage of mitotic cells that overcame the checkpoint arrest after bosutinib-isomer treatment was ~4-fold higher than achieved with the use of UCN-01. Thus, it is believed that the bosutinib-isomer may be a more effective inhibitor of the DNA damage checkpoint than UCN-01.

The mitotic defect was next examined at higher resolution in cells that were treated with gemcitabine+bosutinib isomer (Formula II), and compared them to gemcitabine+UCN-01. It was observed that overriding the gemcitabine induced S phase checkpoint arrest with Chk1 inhibitors (UCN-01) results in a discrete and reproducible mitotic defect called MUGs (mitotically unreplicated genomes). The defining feature of MUGs is the unreplicated centromeres in the genome are physically detached from the chromosome mass (FIG. 4).

Normally, microtubules from opposite spindle poles bind to proteins that are recruited to the replicated centromere, and facilitate the separation of sister chromatids at the onset of anaphase. For MUGs, the microtubules are haphazardly attached to the unreplicated centromere and the opposing forces will tear the centromere complex away from the bulk of the chromosomes. The chromosome mass that are no longer attached to microtubules occupies two lobes that lie outside of the spindle, as opposed to a normal metaphase where all the chromosomes lie between the two spindle poles. The fragmented centromere can be visualized after staining for the CENP-F kinetochore protein. The bosutinib-isomer clearly overrides the gemcitabine-induced S phase arrest in a manner that is virtually indistinguishable from UCN-01 (FIG. 4).

Figure 6:
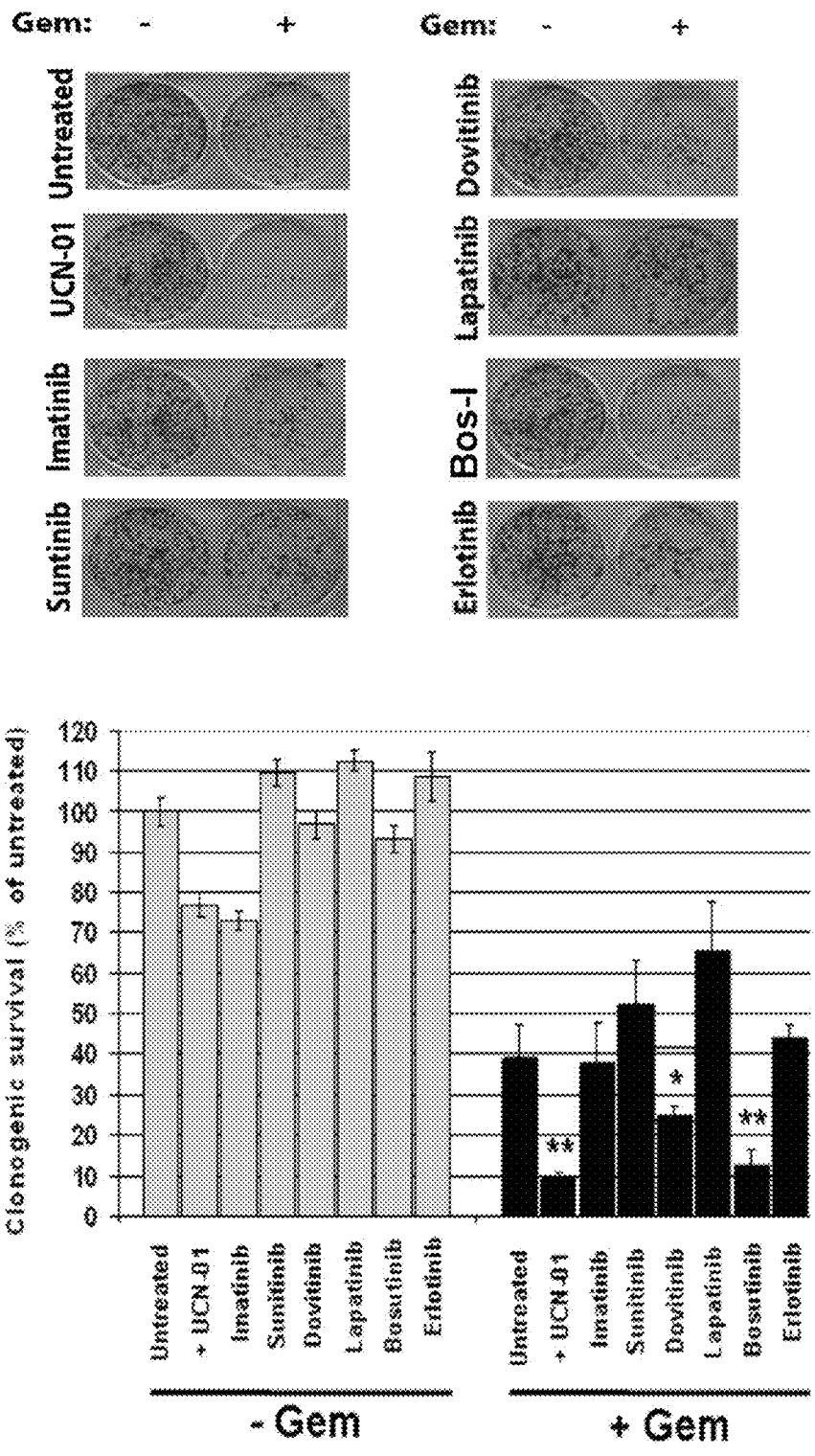
FIG. 6 shows the results of clonogenic assay performed on PANC1 cells treated with and without gemcitabine (10 nM) for 24 h before the addition of indicated compounds (all at 1 µM) or UCN-01 (100 nM) for a further 3 h. After this time all drugs were removed and cells were plated to determine their efficiency of colony formation after 10 days.

Although bosutinib-isomer was synthesized as an inhibitor of src/abl tyrosine kinases, a published report that surveyed the activities of a panel of kinase inhibitors against a panel of 300 recombinant human protein kinases, showed that the activities of 84 kinases were inhibited by more than 50%. Anastassiadis T et al. (2011) Nature Biotechnology. 29:1039-45. FIG. 5 presents this information for all of the tyrosine kinase inhibitors that were tested in FIG. 1. Among the 84 kinase targets inhibited by bosutinib-isomer are the Chk1 and Wee1 kinases that are critical for cell cycle checkpoint arrest induced by DNA damage. Dovitinib and sunitinib inhibited Chk1 to a similar degree as bosutinib-isomer, but neither drug inhibited Wee1 kinase. In cells, sunitinib exhibited no sensitizer activity to gemcitabine (FIG. 1), did not override the gemcitabine induced S phase arrest as determined by time-lapse studies (FIG. 3). Dovitinib exhibited a very mild sensitizer activity that correlated with very modest ability to induce checkpoint override (FIG. 6). It is hypothesized that the dual inhibition of Chk1 and Wee1 by bosutinib-isomer is responsible for its potent sensitizing activity.

The bosutinib-isomer (Formula II) has unique biochemical and biological properties provides greater potency to Chk1 and Wee1 as compared to authentic bosutinib. It is believed that these unique properties may be attributed to the 3,5, dichloro-4-methoxy groups on the aniline ring that are absent from bosutinib. It is further believed that additional chemical structures with modifications at the 3,4,5 positions in the aniline ring may also exert gemcitabine sensitization properties that maybe used to improve treatment outcomes of cancer patients.

The invention is not limited to the embodiments described and exemplified above, but is capable of variation and modification within the scope of the appended claims.

We claim:

1. A method for treating a tumor in a subject in need thereof, comprising inducing DNA damage in a cell of the tumor, and administering to the subject an effective amount of a bosutinib isomer of Formula II:

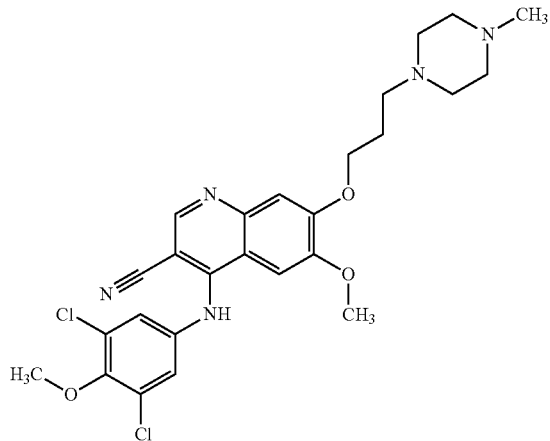

(II), or a pharmaceutically acceptable salt thereof, thereby treating the tumor.

2. The method of claim 1, wherein inducing DNA damage in the cell comprises irradiating the cell in the subject.

3. The method of claim 1, wherein inducing DNA damage in the cell comprises administering to the subject an effective amount of an agent that damages DNA.

4. The method of claim 3, wherein the agent comprises an alkylating agent.

5. The method of claim 3, wherein the agent comprises a pyrimidine analog.

6. The method of claim 3, wherein the agent comprises gemcitabine.

7. The method of claim 1, wherein the tumor is a tumor of the pancreas, lung, head and neck, kidney, hematopoietic system, breast, ovary, colon, lymph nodes, bladder, prostate gland, stomach, or esophagus.

8. The method of claim 6, wherein the bosutinib isomer of Formula II reduces the $LC_{50}$ of gemcitabine to less than about 10 nM.

9. The method of claim 6, wherein the bosutinib isomer of Formula II reduces the $LC_{50}$ of gemcitabine to less than about 5 nM.

10. The method of claim 6, wherein the bosutinib isomer of Formula II reduces the $LC_{50}$ of gemcitabine to about 3 nM or less.

11. A method for treating a tumor in a subject in need thereof, comprising inducing DNA damage in a cell of the tumor, and administering to the subject an effective amount of a bosutinib isomer of Formula IV:

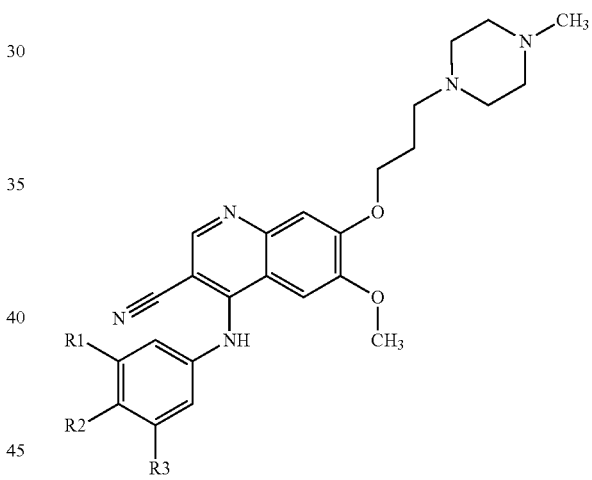

(IV), or a pharmaceutically acceptable salt thereof, wherein each of $R_1$ and $R_3$ is independently selected from the group consisting of F, Br, and I, and wherein $R_2$ is selected from the group consisting of H and N, thereby treating the tumor.

12. The method of claim 11, wherein inducing DNA damage in the cell comprises irradiating the cell in the subject.

13. The method of claim 11, wherein inducing DNA damage in the cell comprises administering to the subject an effective amount of an agent that damages DNA.

14. The method of claim 13, wherein the agent comprises an alkylating agent.

15. The method of claim 13, wherein the agent comprises a pyrimidine analog.

16. The method of claim 13, wherein the agent comprises gemcitabine.

17. The method of claim 11, wherein the tumor is a tumor of the pancreas, lung, head and neck, kidney, hematopoietic system, breast, ovary, colon, lymph nodes, bladder, prostate gland, stomach, or esophagus.

18. The method of claim 1, wherein the tumor is a tumor of the pancreas.

19. The method of claim 6, wherein the tumor is a tumor of the pancreas.

20. The method of claim 11, wherein the tumor is a tumor of the pancreas.

21. The method of claim 16, wherein the tumor is a tumor of the pancreas.

* * * * *